United States Patent [19]

Hayashi

[11] Patent Number: 5,627,307

[45] Date of Patent: May 6, 1997

[54] METHOD FOR MEASURING INTENSITY INDEX OF ODOR

[75] Inventor: Yoshikazu Hayashi, Inuyama, Japan

[73] Assignee: Fortec Co., Ltd., Aichi, Japan

[21] Appl. No.: 559,838

[22] Filed: Nov. 20, 1995

[51] Int. Cl.$^6$ .............................. G01N 27/00; G01N 1/00
[52] U.S. Cl. ............................................................ 73/23.34
[58] Field of Search ............................. 73/23.34; 422/83, 422/88

[56]  References Cited

U.S. PATENT DOCUMENTS

| | | | |
|---|---|---|---|
| 3,882,713 | 5/1975 | Nishida et al. | 73/23.34 |
| 4,520,651 | 6/1985 | Litman | 73/23.34 |
| 5,106,755 | 4/1992 | Tanaka | 73/23.34 |

FOREIGN PATENT DOCUMENTS

| | | | |
|---|---|---|---|
| 143954 | 6/1989 | Japan | 73/23.34 |
| 272361 | 11/1990 | Japan . | |

OTHER PUBLICATIONS

Electronics Ceramics dated Jul. 1986, pp. 21–24 titled Odor Sensor (Translation of paragraph 3 is attached herewith.).

*Primary Examiner*—Hezron E. Williams
*Assistant Examiner*—Daniel S. Larkin

[57]  ABSTRACT

An odor intensity index measuring apparatus is provided for measuring odor intensity objectively and easily for various types of odor. Sample air is diluted with odorless air at a desired scale factor in a dilution unit. The diluted air is fed through an air duct to an odorometer. Corresponding to the intensity of odor, voltage V is emitted from the odorometer. In an electronic control unit, the scale factor at which sample air is diluted by the dilution unit is gradually increased. The dilution scale factor which is reached when the output voltage from the odorometer becomes lower than the specified value indicating the odorless condition is displayed on a liquid crystal display. Like the conventional three bag odor comparison method, the odor intensity index can be measured in the same manner for various types of odor. Different from the conventional method, the degree of the odor intensity can be measured objectively without relying on the human sense of smell.

7 Claims, 3 Drawing Sheets

METHOD FOR MEASURING INTENSITY INDEX OF ODOR

FIELD OF THE INVENTION

This invention relates to a method for measuring intensity index of odor of sample gas.

BACKGROUND OF THE INVENTION

Recently, in addition to noise and air pollution, malodor became an issue of public nuisance. Conventionally, the intensity of odor is measured through instrumental analysis or in three bag odor comparison method described later.

In the three bag odor comparison method, three bags are filled with odorless air. Odorless air is prepared by activated carbon treatment of standard air, for example, air on Hirugano plateau, which is famous for its clean atmosphere in Japan. Subsequently, sample air is mixed into one of the three bags. Each air filling these three bags is smelled by six panelists, respectively, to see which bag smells. The concentration of sample air to be mixed in the bag is gradually decreased, until only 50% or less of the panelists have the right answer. By the concentration of sample air at the moment, the intensity of odor, i.e. odor concentration is measured. In the three bag odor comparison method, the odor concentration is measured in the same way for various types of odor.

In the three bag odor comparison method, however, the resulting odor concentration cannot be an objective index because persons have individual variation in their perception of odor. If they smell the same odor many times in one day, their perception to the odor will often vary between the first time and the last time. Also through the instrumental analysis, odor concentration cannot be easily measured, because sensor outputs differ in properties from one another with substances to be measured.

Recently, an odor sensor was developed using a ceramic sensor sensitive to oxidizing gas or reducing gas (refer to Electronics Ceramics July 1986, pages 21-24). The correspondence of the odor sensor's sensitivity to sample air to the dilution scale factor resulting from the aforementioned three bag odor comparison method varies with odor types and odor producing substances. No pure coincidence is seen between the sensor's sensitivity and the dilution scale factor by panelists. Some odor hardly changes even if diluted and other odor changes largely when diluted.

SUMMARY OF THE INVENTION

Wherefore, an object of the present invention is to provide an odor intensity index measuring method with which practical odor intensity can be objectively and easily measured for all the types of odor.

Another object of the invention is provide an inventive and practical apparatus for measuring an odor intensity index.

The odor intensity index mentioned herein is a dilution scale factor of sample gas obtained when the odor intensity measured with a sensor nearly equals that of odorless air while the sample gas is diluted with the odorless air.

In a method of measuring an odor intensity index according to the invention with a testing chamber and an odor sensor, sample gas the odor of which is to be measured is introduced into the chamber. While the sample gas is repeatedly diluted with odorless air, every time the sample gas is diluted, a dilution scale factor is updated. Subsequently, odor intensity is measured with the odor sensor at every dilution. It is then determined whether or not measured odor intensity becomes lower than a predetermined odor intensity. When the measured odor intensity lowers than the predetermined odor intensity, the updated dilution scale factor is notified as an odor intensity index.

The odor intensity index measuring apparatus according to the present invention is composed of an odor measurement unit for measuring odor intensity in a measuring atmosphere, a partial pressure change unit for changing the partial pressure of sample gas in the atmosphere, a detection unit for detecting the point at which a value measured by the odor measurement unit has crossed a specified value, and a notifying unit for notifying either one of the partial pressure and the dilution scale factor corresponding to the partial pressure of sample gas detected at the point by the detection unit.

In the present invention, the odor intensity index can be measured in the same manner for various types of odor, like the three bag odor comparison method. Furthermore, in the present invention, different from the three bag odor comparison method, human sense of smell does not have to be relied upon. Consequently, the odor intensity index can be objectively measured.

BRIEF DESCRIPTION OF THE DRAWINGS

The invention will now be described, by way of example, with reference to the drawings, in which.

DETAILED DESCRIPTION OF THE PREFERRED EMBODIMENTS

Figure 1:
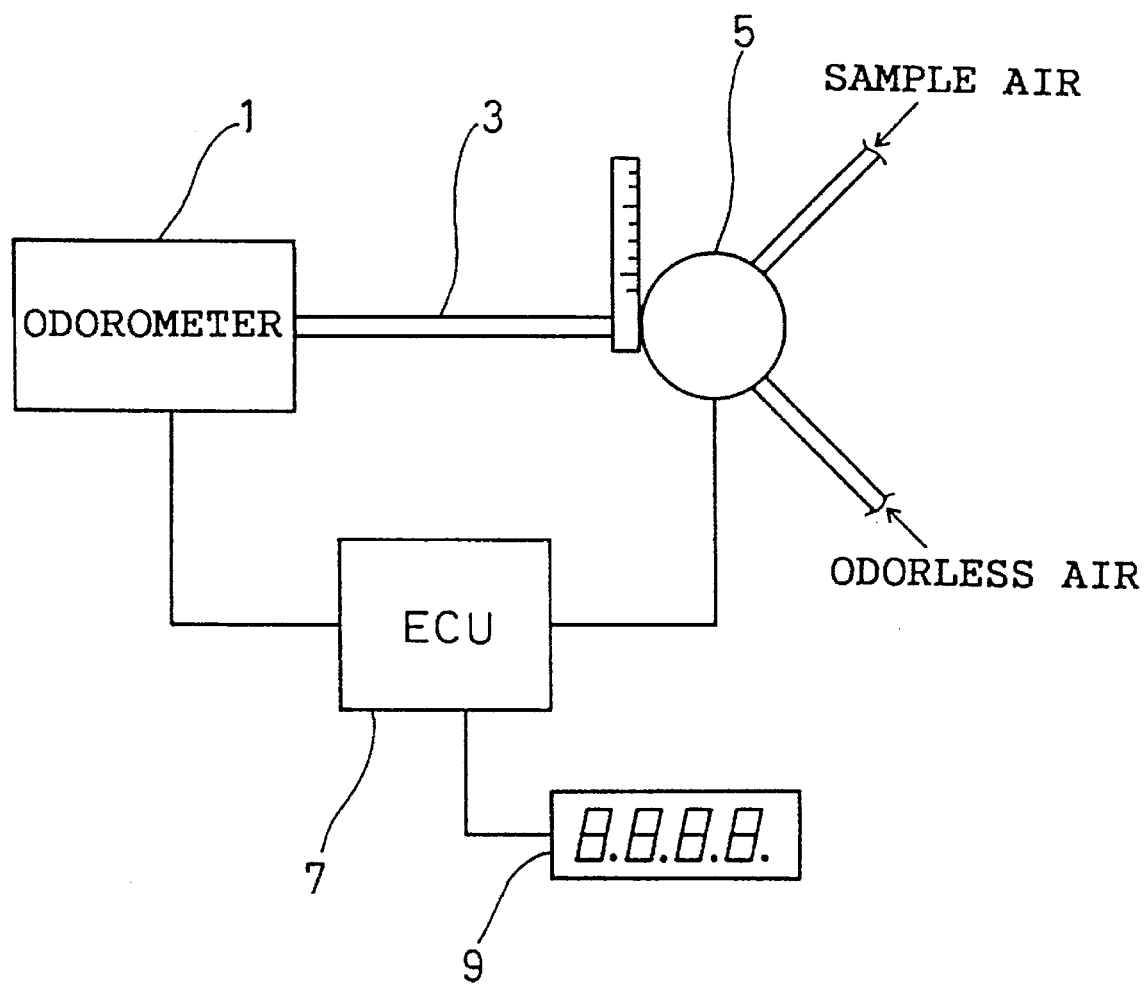
FIG. 1 is a diagrammatic representation of the odor intensity index measuring apparatus embodying the present invention.

As shown in FIG. 1, the odor intensity index measuring apparatus of the embodiment is provided with an odorometer 1, for example, an odorometer having tradename of Aerabuster manufactured by Kabushiki Kaisha B&H Labo, and a dilution unit 5, for example, a standard gas divider having tradename of SGD-XC manufactured by Kabushiki Kaisha Estech. In the dilution unit 5 sample air is diluted at a specified scale factor by introducing odorless air. The diluted sample air is fed from the dilution unit 5 through an air pipe 3 to the measuring atmosphere in which the odorometer 1 is positioned. The odor in the atmosphere is measured by the odorometer 1, and voltage V is emitted corresponding to the intensity of odor from the odorometer 1.

The odorometer 1 and the dilution unit 5 are connected to an electronic control unit 7. The electronic control unit 7 is connected to a liquid crystal display 9 for indicating the scale factor at which sample air is diluted to yield almost no odor. Drive signal is transmitted from the electronic control unit 7 to the dilution unit 5 such that the dilution scale factor of sample air is changed, and output voltage V from the odorometer 1 is read by electronic control unit 7. The dilution scale factor at which the output voltage V becomes lower than a specified voltage Vo representing odorless condition is indicated on the screen of the liquid crystal display 9.

Figure 2:
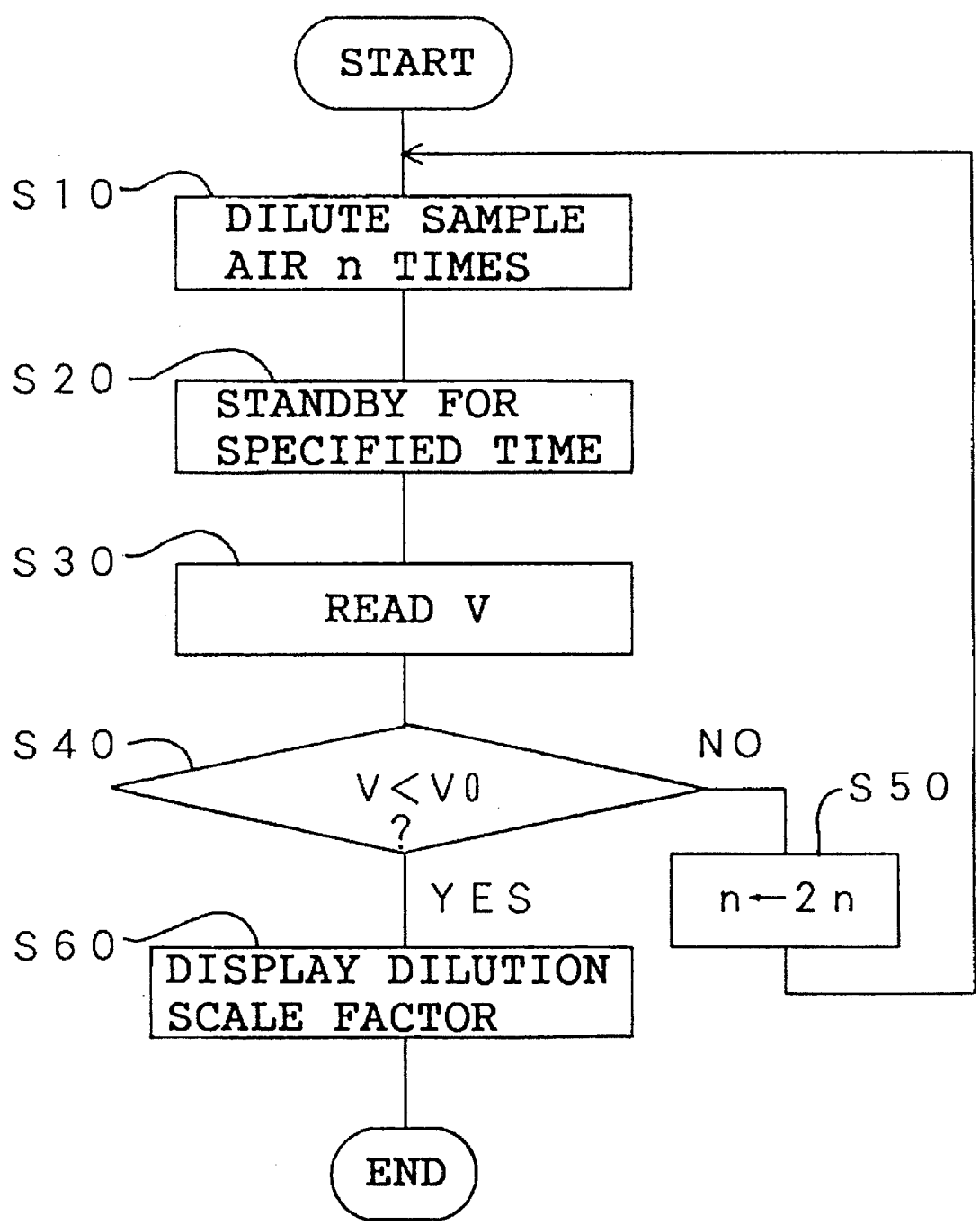
FIG. 2 is a flow chart showing the progress of process executed by an electronic control circuit mounted on the odor intensity index measuring apparatus.

The process of electronic control unit 7 is now explained referring to the flowchart of FIG. 2. The process is initiated by the electronic control unit 7 when an initial value of dilution scale factor n is established and a not-shown measurement start button is depressed.

After the process is started, first at step S10 drive signal is transmitted from the electronic control unit 7 to the dilution unit 5, such that sample air is diluted "n" times by introducing odorless air into the dilution unit 5. Subsequently, at step S20 the electronic control unit 7 is on standby for a specified period of time until a chamber of the odorometer 1 is filled with the n-times diluted sample air. When the specified period of time has elapsed, the process proceeds next to step S30, at which the output voltage V from the odorometer 1 is read. Subsequently, it is determined at step S40 whether or not the output voltage V is lower than the specified voltage Vo. When it is determined in the negative that the output voltage V is equal to or larger than the specified voltage Vo, the process proceeds next to step S50, at which the dilution scale factor n is changed to 2n and the process goes back to step S10. Then, the same process steps are executed using the dilution scale factor twice as much as the previous dilution scale factor.

Subsequently, while the dilution scale factor at which sample air is diluted is gradually increased, the process steps S10 through S50 are repeatedly executed. When a certain dilution scale factor is reached, the diluted sample air becomes almost odorless. In this case, it is determined in the affirmative at step S40 that the output voltage V is lower than the specified voltage Vo, and the process goes to step S60, at which the dilution scale factor at the moment is indicated on the liquid crystal display 9, thereby ending the process.

Figure 3:
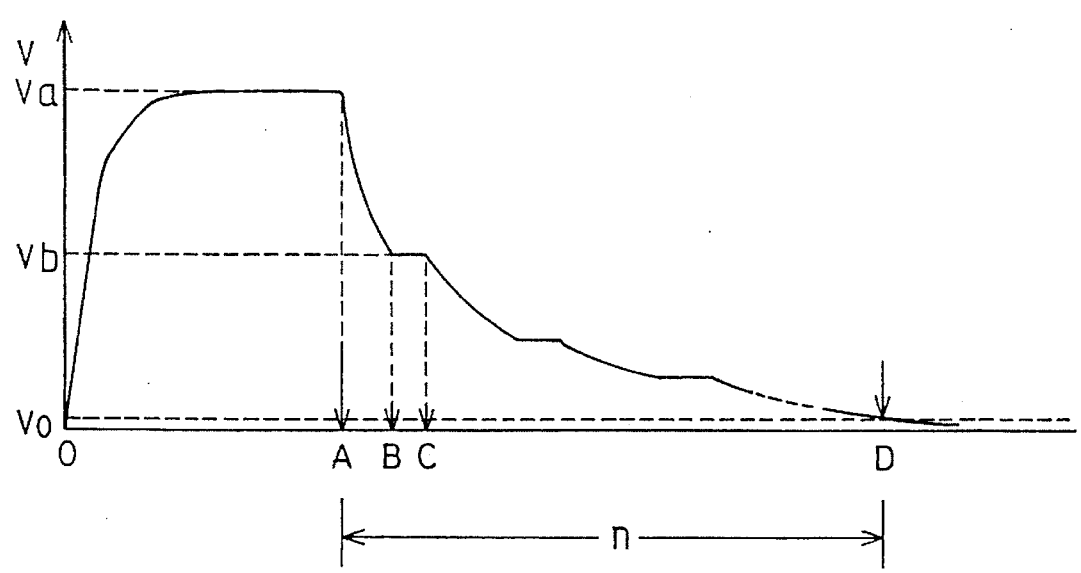
FIG. 3 is a graph indicating sensor outputs obtained when odor intensity index is measured using the odor intensity index measuring apparatus shown in FIG. 1.

As shown in FIG. 3, sensor output is zero before sample gas is introduced into a chamber of dilution unit 5. After sample gas is introduced, sensor output is increased up to value Va. When a predetermined volume of odorless air is introduced into the chamber of dilution unit 5 starting from time point A in order to dilute sample gas, sensor output is decreased down to value Vb at time point B, i.e. a first dilution point. The period of time elapsed between points B and C corresponds to the specified period of time for which the electronic control unit 7 is on standby. These procedures are repeated until the sensor output becomes lower than value Vo at point D, thereby ending the procedure. The value Vo is the upper limitation at which sample gas is determined to be odorless. The sensor output at which sample gas is determined to be odorless can be predetermined by multiple panelists' conducting an organoleptic test. In this way the dilution scale factor n at which sample gas is diluted from time point A till time point D is obtained as an index of sample gas intensity.

The graph shown in FIG. 3 shows a result of measuring odor intensity of the components evaporated from soy sauce. Various types of odor were measured using the odor intensity index measuring apparatus. The result was that the characteristic of sensor output varied with the types of odor, and that even if any type of odor is measured, however, the sensor output shows the value lower than the predetermined value at the end of dilution. Consequently, for any type of odor, the dilution scale factor can be obtained.

As aforementioned, in the odor intensity index measuring apparatus of the embodiment, the dilution scale factor which is reached when the output voltage V from the odorometer 1 becomes lower than the specified voltage Vo is indicated on the liquid crystal display 9. Therefore, the degree of the odor intensity in sample air can be easily detected. In the embodiment, the intensity of various types of odor can be easily measured in the same manner, like the conventional three bag odor comparison method. Furthermore, in the embodiment, the odor intensity index can be objectively measured without relying on the human sense of smell, different from the conventional method.

The signal identical to the signal transmitted to the liquid crystal display 9 by the electronic control unit 7 in the embodiment can be transmitted to other not-shown units, such that the measured odor intensity index can be processed in various manners. For example, when the signal is transmitted to a not-shown printer, the odor intensity index can be recorded. By transmitting the signal to another not-shown electronic control unit, various computation processes can be executed using the data of odor intensity index.

In the aforementioned embodiment, the odorometer 1 forms the odor measurement unit, the dilution unit 5 forms the partial pressure change unit, the electronic control unit 7 forms a detection or output unit, and the liquid crystal display 9 forms the notifying unit.

In the embodiment, the dilution scale factor of sample air is gradually increased. Alternatively, the initial value n of the dilution scale factor is set as a sufficiently large value, and the dilution scale factor is then decreased gradually until the output voltage V becomes lower than the specified voltage Vo. In such a modification, a smaller amount of sample air can be used for measurement of odor intensity.

In the embodiment, the dilution scale factor of sample air is changed by the dilution unit 5. Since the voltage V varies with the partial pressure of sample air in the measurement atmosphere, however, the measurement atmosphere can be sealedly connected to, for example, an air cylinder, such that the odor intensity index can be measured by varying the atmospheric pressure in the measurement atmosphere. In this modification, the atmospheric pressure which is reached when the voltage V becomes lower than the specified voltage can be indicated on the liquid crystal display 9.

In the embodiment, the dilution scale factor is changed by the dilution unit 5 driven by the electronic control unit 7. A switch for establishing the dilution scale factor can be attached to the dilution unit 5. In such a modified embodiment, a pilot lamp, buzzer or other alarm is connected to the electronic control unit 7. The alarm is driven when the output voltage V from the odorometer becomes lower than the specified voltage Vo. The switch is operated to gradually increase the dilution scale factor, and when the alarm is driven, the position of the switch is read, by which the odor intensity index can be measured. In this modified embodiment, the structure of the measuring apparatus can be simplified, thereby reducing the manufacture cost.

Moreover, the odor intensity index measuring apparatus of the embodiment can be used for measuring the odor intensity index of sample gas including no air.

In the odor intensity measuring method of the invention, the dilution scale factor at which the odor intensity measured with a sensor nearly equals that of odorless air while sample gas is being diluted with odorless air is measured. Therefore, the degree of objective odor intensity can be grasped for any type of odor, independently of human perception to odor.

As aforementioned, in the odor intensity index measuring apparatus according to the invention, by using the partial pressure which sample gas exerts when the value measured by the odor measurement unit crosses the specified value, and by mounting the notifying unit for notifying the partial pressure or diluted concentration of sample gas detected by the detection unit, the odor intensity can be easily obtained.

Consequently, the odor intensity can be measured in the same manner for multiple types of odor in the invention, like the known three bag odor comparison method. However, different from the three bag odor comparison method, in the invention the odor intensity index can be measured objectively without relying on the human sense of smell.

Moreover, by mounting the output unit for emitting the partial pressure or odor intensity index of sample gas, the odor intensity index can be entered into various units for processing.

This invention has been described above with reference to the preferred embodiment as shown in the figures. Modifications and alterations may become apparent to one skilled in the art upon reading and understanding the specification. Despite the use of the embodiment for illustration purposes, the invention is intended to include all such modifications and alterations within the spirit and scope of the appended claims.

What is claimed is:

1. A method of measuring odor intensity index with a testing chamber and an odor sensor comprising the steps of:

introducing sample gas the odor of which is to be measured into said chamber;

repeatedly diluting sample gas with odorless air;

updating a dilution scale factor every time sample gas is diluted;

measuring odor intensity with said odor sensor every time sample gas is diluted;

determining whether or not measured odor intensity becomes lower than a predetermined odor intensity; and notifying the updated dilution scale factor as an odor intensity index when the measured odor intensity becomes lower than the predetermined odor intensity.

2. A method according to claim 1, wherein said step of diluting sample gas includes a step of filling said chamber with diluted sample gas.

3. A method according to claim 1, wherein said step of diluting sample gas includes a step of increasing the pressure of said chamber by introducing odorless air into said chamber.

4. A method according to claim 1, wherein said step of repeatedly diluting sample gas includes a first step of diluting sample gas at a relatively large dilution scale factor and a second step, subsequent to said first step, of diluting sample gas at a relatively small dilution scale factor.

5. An odor intensity index measuring apparatus comprising:

odor measurement means for measuring odor intensity in a measuring atmosphere;

partial pressure change means for changing the partial pressure of sample gas in the atmosphere;

detection means for detecting the point where a value measured by said odor measurement means crosses a specified value; and notifying means for notifying either one of the partial pressure and the dilution scale factor corresponding to the partial pressure of sample gas detected at said point by said detection means.

6. An odor intensity index measuring apparatus according to claim 5, wherein said partial pressure change means includes means for diluting the sample gas with odorless air.

7. An odor intensity index measuring apparatus according to claim 5 further comprising output means for outputting either one of the partial pressure and the dilution scale factor of sample gas detected at said point by said detection means.

* * * * *